(12) United States Patent
Rhodes (10) Patent No.: US 7,235,268 B2
(45) Date of Patent: Jun. 26, 2007

(54) TREATMENT OF INFLAMMATORY BOWEL DISEASE

(75) Inventor: Jonathan Rhodes, Liverpool (GB)

(73) Assignee: Provexis (IBD) Limited, Manchester (GB)

( * ) Notice: Subject to any disclaimer, the term of this patent is extended or adjusted under 35 U.S.C. 154(b) by 0 days.

(21) Appl. No.: 10/542,875

(22) PCT Filed: Feb. 10, 2004

(86) PCT No.: PCT/GB2004/000521

§ 371 (c)(1),
(2), (4) Date: Jul. 20, 2005

(87) PCT Pub. No.: WO2004/069143

PCT Pub. Date: Aug. 19, 2004

(65) Prior Publication Data

US 2006/0134247 A1    Jun. 22, 2006

(30) Foreign Application Priority Data

Feb. 10, 2003 (GB) ................................ 0302872.7

(51) Int. Cl.
*A61K 36/68* (2006.01)
(52) U.S. Cl. .................................... 424/738
(58) Field of Classification Search ...................... None
See application file for complete search history.

(56) References Cited

U.S. PATENT DOCUMENTS

| 4,921,804 | A | * | 5/1990 | Wu | ............................. | 435/189 |
| 5,234,706 | A | * | 8/1993 | Slimak | ....................... | 426/549 |
| 5,510,337 | A | * | 4/1996 | Aritsuka | ...................... | 514/57 |
| 2001/0046526 | A1 | * | 11/2001 | Greenfelder | ................ | 424/779 |

OTHER PUBLICATIONS

Campos et al. Inflammatory Bowel Diseases. Principals of Nutritional Therapy. 2002. Rev. Hosp. Clin Fac. Med. S. Paulo. pp. 187-198.*
Tayo N. Fagbemi. Effect of blanching and ripening on functional properties of plantain (*Musa aab*) flour. 1999. Plant foods for human nutrition. pp. 261-269.*
1997. Tanya et al. Soluble and insoluble fiber contents of some Cameroonian foodstuffs. Plant Foods for Human Nutrition. 51: 199-207.*

* cited by examiner

*Primary Examiner*—Christopher R. Tate
*Assistant Examiner*—Melenie McCormick
(74) *Attorney, Agent, or Firm*—Seth D. Levy; Davis Wright Tremaine LLP (57) ABSTRACT

The present invention relates to compositions (including medicaments and nutritional products) for use in the prevention or treatment of Inflammatory Bowel Disease. Such compositions comprise a therapeutically effective amount of a soluble fibre derivable from fruit of the *Musa* spp. The soluble fibre may in particular be derived from plantains or bananas.

29 Claims, 4 Drawing Sheets

TREATMENT OF INFLAMMATORY BOWEL DISEASE

This application is the National Phase of International Application PCT/GB2004/000521, filed Feb. 10, 2004, which designated the U.S. and that International Application was published under PCT Article 21(2) in English. This application also includes a claim of priority under 35 U.S.C. §119(a) and §365(b) to British patent application No. GB 0302872.7, filed Feb. 10, 2003.

The present invention relates to the treatment of inflammatory bowel disease (IBD) and in particular treatment of IBD with soluble extracts derived from edible plants.

IBD is a term used to describe idiopathic, chronic inflammation of the gastrointestinal tract and includes two main phenotypes: Crohn's disease (CD) and ulcerative colitis (UC). Crohn's disease is typified by granulomatous inflammation affecting any part of the gastrointestinal tract but particularly the ileocecal area. Ulcerative colitis is colon-specific and is associated with extensive epithelial damage, crypt abscesses and abundant mucosal neutrophils. Patients with extensive UC or colonic Crohn's disease have an approximately ten-fold increased risk of developing colorectal cancer, which represents the major cause of IBD-associated mortality.

The aetiology of IBD is still not well understood. There is however a growing consensus based both on patient studies and from transgenic animal models of colitis that the intestinal inflammation results from an abnormal response to non-pathogenic intestinal bacteria. Some of the most striking evidence for the involvement of bacteria in IBD pathogenesis comes from studies demonstrating the presence of *E. coli* in ileal mucosal biopsies taken from Crohn's disease patients. These organisms, despite lacking conventional markers of bacterial pathogenicity, are able to invade intestinal cell lines and to live within macrophages without inducing apoptosis. Other studies, which used a broad-specificity 16S ribosomal probe for in situ hybridisation to detect bacteria of all species, found an increase in unidentified bacteria within the mucus layer in both UC and CD.

Given the debilitating nature of IBD, as well as IBD-associated mortality, there is a need to provide new and improved treatments for these conditions. It is therefore an object of the present invention to provide compositions useful in the prevention or treatment of IBD.

According to a first aspect of the present invention, there is provided a composition for use in the prevention or treatment of Inflammatory Bowel Disease comprising a therapeutically effective amount of a soluble fibre derivable from fruit of the *Musa* spp.

According to a second aspect of the present invention, there is provided the use of soluble fibre derivable from fruit of the *Musa* spp. for the manufacture of a medicament for the prevention or treatment of Inflammatory Bowel Disease.

According to a third aspect of the present invention, there is provided a method for the treatment of Inflammatory Bowel Disease comprising administering to a subject in need of such treatment a therapeutically effective amount of a a soluble fibre derivable from fruit of the *Musa* spp.

By "soluble fibre" we mean fibres capable of being dissolved in an aqueous medium (and also optionally the bloodstream) that comprise soluble polysaccharides or oligosaccharides from a non-starch source. Such fibres are capable of passing through the stomach and small intestine to the large intestine without being substantially digested. The fibres may then act as a fermentable substrate for bacteria in the large intestine. Different types of soluble fibre may be derived from common food sources such as fruits, especially apples and oranges; vegetables; oat bran; barley; and legumes. Soluble fibres from different sources will contain varying amounts of polysaccharides such as hemi-celluloses or pectins, as well as varying amounts of oligosaccharides and monosaccharide derivatives. While the composition of soluble fibre is characteristic of the plant source, it will vary in response to factors such as cultivar, ripeness and geographical origin. In contrast, insoluble fibres are found in the cell wall of plants and give the plant structure. A common food source of insoluble fibre is wheat bran and fruits with edible skins and seeds, such as strawberries. Insoluble fibres aid digestion. They primarily act as bulking agent (resulting in shorter transit time and increased faecal mass); and also hold on to water as they move through the intestinal tract (softening the stools and thereby helping prevent constipation).

It will be appreciated that soluble fibre according to the present invention may be in pure form or alternatively it may also be mixed with other compounds (provided those compounds do not inhibit the anti-inflammatory properties of fibre according to the invention). Accordingly the present invention encompasses compositions comprising effective amounts of soluble fibre as-well-as insoluble fibre.

It is preferred that the soluble fibre used according to the invention is non-gelling.

Although we do not wish to be bound by any hypothesis the inventor believes that soluble fibres are useful in the treatment and prevention of IBD based upon their understanding of this scientific field and the work presented in Example 1.

He has recognised that IBD (e.g. ulcerative colitis and Crohn's disease) may represent an altered response to the normal intestinal microbial flora. In particular, he believes there is a possibility that apparently non-pathogenic "harmless" bacteria can cause inflammation if they penetrate the layer of mucus that coats the intestine and associate themselves closely with the lining cells of the intestine. A critical step in bacterial colonisation of the gut is adherence of the bacterium to the mucosa through fimbrial- and/or surface proteins known as adhesins. These proteins act as lectins recognising glycosyl motifs expressed by host cell-surface glycolipid or glycoprotein and play a key role in bacterial pathogenicity. Aberrant glycosylation of mucosal glycoproteins has been demonstrated in colonic disease, with similar abnormalities having been found in ulcerative colitis, Crohn's disease and colon cancer. The inventor believes that there may be a sub-group of bacteria with adhesins specific to the carbohydrate structures that are expressed in inflammatory bowel disease mucosa. Thus the altered glycosylation of colonic mucosal glycoproteins seen in IBD may represent receptors for specific adhesins of the *E. coli* associated with early inflammatory bowel lesions.

The inventor therefore characterised adherence of inflammatory bowel disease-related bacteria to carbohydrate structures (see Example 1). He found that the adhesion of such bacteria to cell surfaces can be blocked by some, but not all, complex carbohydrates. In particular he found that soluble fibres according to the invention were effective for preventing bacterial adhesion and accordingly have efficacy for preventing or treating IBD. Accordingly, it is believed that the soluble fibres may either mimic or compete with bacterial receptors, thus preventing bacterial recruitment and subsequent inflammation.

Soluble fibre according to the present invention may be derived from low molecular weight partially hydrolysed gums (e.g. guar gum, locust bean gum, fenugreek gum or okra gum and other suitable low viscosity edible gums), bovine submaxillary mucin (BSM), alginate or partially hydrolyzed carrageenan.

Soluble fibre according to the present invention may also be derived from a fruit, vegetable or cereal extract or an active fraction thereof. The active fraction may be derived from a fruit or grain selected from fruit or plants of the families Solanaceae, Rutaceae, Cucurbitaceae, Rosaceae, Musaceae, Anacardiaceae, Vitacease, Arecaceae, Ericaceae, Lauraceae and Poaceae.

Examples of fruits that can be used in accordance with the present invention are those selected from the families Solanaceae, Rutaceae, Cucurbitaceae, Rosaceae, Musaceae, Anacardiaceae, Bromeliaceae, Vitaceae, Arecaceae, Ericaceae and Lauraceae.

Examples of Solanaceae include the tomato, for example the English tomato variety. Examples of Rutaceae include the *Citrus* species such as *Citrus paradisii* (grapefruit), *Citrus sinensis* (orange), *Citrus limon* (lemon) and *Citrus aurantifolia* (lime). Examples of Cucurbitaceae include *Cucumis melo* (melon), e.g. the honeydew melon. Examples of Anacardiaceae include *Mangifera indica* (mango). Examples of Rosaceae include *Pyrus sylvestris* (apple), *Pyrus communis* (pear), *Anygdalus perisca* or *Prunus persica* Var. *nectarina* (nectarine), *Prunus armeniaca* (apricot), *Prunus domestica* (plum), *Prunus avium* (cherry), *Prunus persica* (peach), the strawberry and the blackberry. Examples of Musaceae include *Musa paradisiaca* (banana). Examples of Bromeliaceae include *Ananas sativus* (pineapple). Examples of Lauraceae include *Persea gratisssima* or *Persea americana* (avocado). Examples of Vitaceae include *Vitis vinifera* (grape). Examples of Arecaceae include *Phoenix dactylifera* (date). Examples of Ericaceae include the blueberry.

Particular examples of fruits, the extracts or active fractions of which have been found to be useful according to the invention are the tomato, grapefruit, melon, mango, nectarine, strawberry, plum, grape, pear, apple and avocado. Particular examples of vegetables are the potato, carrot, parsnip, turnip, squash, courgettes and bell peppers. Particular examples of cereals are wheat grains, barley grains, maize kernels and rice grains.

However the inventors have found that soluble fibres derived from the Musaceae family (i.e the *Musa* and *Ensete* genera) are particularly useful. Soluble fibres from the *Musa* spp (i.e bananas or plantain) have most efficacy for treating or preventing IBD. Eleven *Musa* species are known but the soluble fibres are preferably derived from the cultivars *Musa acuminata, Musa balbisiana, Musa paradisiaca* or *Musa sapientum.*

A preferred soluble fibre for use in treating or preventing IBD is derived from plantain or green (i.e. unripe) edible bananas.

Soluble fibre according to the invention may be prepared in its simplest form by homogenising a source of the fibre (e.g. plantain flesh) in an aqueous solution and then decanting off the aqueous supernatant. This supernatant may then be used according to the invention. Alternatively the mixture may be centrifuged to separate solids from the aqueous solution comprising the soluble fibre. This aqueous solution may consist essentially of the juice of the fruit, optionally with the addition of extra water added during the homogenising step. Such aqueous extracts can be concentrated, enriched or condensed by, for example, standard techniques, e.g. evaporation under reduced pressure. Examples of concentrates are those which are at least 2-fold concentrated, more usually, at least 4-fold, for example at least 8-fold, or at least 40-fold, or at least 100-fold, or at least 200-fold, or at least 1000-fold.

The aqueous solution may be fractionated to isolate one or more active fractions comprising the soluble fibre therein by, for example, molecular weight filtration, or chromatography on a suitable solid support such as a sepharose gel (for size exclusion chromatography) or ion-exchange column using HPLC on a suitably treated silica or alumina, for example ODS coated silica; or by solvent extraction.

Soluble fibre according to the invention may be prepared by following one or more of the followings steps:

(A) It is preferred that the soluble fibre is prepared by mashing or slicing fruit (e.g. plantain or banana) and then boiling the fruit in water (preferably sterile water) for between 2 and 60 minutes, preferably about 30 minutes. Alternatively dried fruit may be milled and then boiled in water as discussed above. These sort of boiling times help to break down starch (the inventor has found that it is undesirable to have a high starch content in the soluble fibres). After boiling, the solution should be centrifuged (e.g. at 10,000 g for 10 minutes) to separate insoluble material from the supernatant. The pellet should then be discarded and the supernatant may be used as soluble fibre according to the present invention. The fact that the supernatant is useful is particularly surprising in the light of the prior art which suggests that the pulp (i.e the pelleted material) may be medically useful. For instance, Rabbini et al. (2001) Gastroenterology 121 p 554–560) suggest banana pulp may be used to treat diarrhoea.

However, it should be appreciated that the inventor has found that boiling at 100° C. is not essential for preparing soluble fibre according to the invention. The examples illustrate that fruit homogenised as described above can produce useable soluble fibre (particularly when steps are taken to remove starch as discussed below) without necessarily boiling the sample.

(B) Preferred soluble fibre may undergo a treatment step with an enzyme capable of hydrolysing starch and thereby removing starch from the soluble fibre. Starch-degrading enzymes such as α-amylases from animal, bacterial or fungal sources, amyloglycosidases or pullulanases may be used for such a purpose, individually or in combination. Accordingly a preferred protocol for producing the soluble fibre involves the soluble fibre being extracted from boiled plantains and being treated with a starch digesting enzyme, or enzymes, to remove starch and produce a Non-Starch Polysaccharide (NSP) fraction.

(C) A further step which may be employed in the preparation and enrichment of soluble fibre according to the invention, is a precipitation step. Such a step may be employed to precipitate the soluble fibre in order that it may be separated from other water soluble contaminants. The precipitated soluble fibre may then be kept in powder form (see below) or alternatively may be resuspended in a liquid of a defined composition and volume (thereby regulating the concentration of the soluble fibre). The inventor has found that an ideal way of precipitating the soluble fibre is to add 80% ethanol to a crude extract of the soluble fibre. As an alterative to precipitation it will be appreciated the dialysis may be employed.

It will be appreciated that the abovementioned steps (A)–(C) for isolating soluble fibre according to the invention may be combined to provide a useful protocol for producing soluble fibre. Such a protocol may comprise:

(1) chop fresh fruit and remove any skins and place in an-aqueous solution; or freeze-dry whole fruit (excluding skins), mill it and place in an aqueous solution; or mill desicated fruit and place in an aqueous solution; or take flour prepared from fruit (e.g. plantain flour) and place in an aqueous solution.

(2) The solution from (1) may then be heated (e.g. boiled at 100° C.) to gelatinise the starch and disperse any starch granules.

(3) The material may also be hydrolysed with starch digesting enzymes to ensure all/most starch is removed.

(4) The remaining liquid fraction comprises Non-Starch Polysaccharides (NSP) which may be used as soluble fibre according to the invention.

(5) The liquid fraction may then be precipitated and washed with 80% ethanol and centrifuged (at about 10,000 g—it will be appreciated that lower centrifugal forces may be employed). The alcoholic supernatant is then discarded and the residue (containing both soluble and insoluble NSP) freeze-dried or spray-dried. The dried product (which also represents soluble fibre according to the invention) may then be stored and reconstituted when desired.

(6) When soluble fibre is required in solution, the dried residue may be boiled in water; centrifuged (e.g. at 10,000 g for 10 mins) and the supernatant used as required.

The supernatant (6) may optionally be freeze or spray dried again to make a preferred (powdered) soluble fibre according to the invention.

A preferred protocol involving the removal of starch and representing a preferred method for producing soluble fibre, comprises:

(i) Plantain skins are removed from plantains and the whole fruit (excluding skins) freeze-dried and then milled.

(ii) The milled material is then boiled (100° C.) for approximately 30 mins in water to gelatinise the starch and disperse any starch granules.

(iii) The material is then hydrolysed with porcine pancreatic amylase (at 40° C.) to ensure almost starch is removed. It is more preferable that soluble fibre for human consumption is treated with bacterial or fungal a-amylase, amyloglucosidase and pullulanase.

(iv) The remaining liquid fraction comprises Non-Starch Polysaccharides (NSP). This is then precipitated and washed with 80% ethanol and centrifuged (at about 10,000 g—it will be appreciated that lower centrifugal forces may be employed). The alcoholic supernatant is then discarded and the residue (containing both soluble and insoluble NSP) spray or freeze-dried. This spray or freeze-dried product (which represents soluble fibre according to the invenion) may then be stored and reconstituted when desired.

(v) When soluble fibre is required in solution, the spray or freeze-dried residue is boiled in water for about 30 mins; centrifuged at 10,000 g for 10 mins and the supernatant used as required.

The supernatant (v) may optionally be freeze dried again to make a preferred (powdered) soluble fibre according to the invention.

The inventor has found that edible matter from plantains (i.e. everything but the skins) constitutes about 50% of the plantain and dry matter constitutes about 31%. The inventors have found that the yield of NSP (following the protocols above) is about 3–4% and about 40% of this NSP represents soluble fibre according to the invention.

The inventor has also found that an effective pH for a soluble fibre solution is around pH 7. An increase in pH increases solubility but excessive alkalinity was found to degrade the polysaccharides or oligosaccharides in the soluble fibre and result in a decrease in efficacy:

Table 1 illustrates the sugar content of a typical soluble fibre obtained according to the steps (i)–(v) of the protocol discussed above. Analysis of the sugar content of a soluble fibre provides a "fingerprint" for soluble fibre from a particular source. It is possible to distinguish between soluble fibre derived from plantain and other plants (e.g. pea-husk or wheat). It will therefore be appreciated that preferred *Musa* derived soluble fibre has a sugar content similar to that given in Table 1.

TABLE 1

| Non-Starch Polysaccharide Constituent Sugars (g/100 g dry matter) | | | | | | | | | |
|---|---|---|---|---|---|---|---|---|---|
| Rhamnose | fucose | Arabinose | Xylose | mannose | galactose | glucose | Glucuronic acid | Galacturonic acid | Total NSP g/100 g |
| 0.1–0.3 | 0.1 | 0.3–0.5 | 0.2 | 0.6 | 0.3–0.5 | 0.9 | 0.1 | 0.8–1.3 | 3.4–4.5 |

It is more preferred that the sugar content is similar to that given in Table 2:

TABLE 2

| Non-Starch Polysaccharide Constituent Sugars (g/100 g dry matter) | | | | | | | | | |
|---|---|---|---|---|---|---|---|---|---|
| Rhamnose | fucose | Arabinose | Xylose | mannose | galactose | glucose | Glucuronic acid | Galacturonic acid | Total NSP g/100 g |
| 0.1 | 0.1 | 0.3 | 0.2 | 0.6 | 0.3 | 0.9 | 0.1 | 0.8 | 3.4 |

Most preferred soluble fibre preparations for use according to the invention are described in the Examples.

IBD may be treated using soluble fibre derived from a natural source (e.g. prepared from Banana or plantain). Alternatively synthetic sugars may be used with the same, or similar composition to the soluble fibre prepared from natural sources.

It will be appreciated that a crude preparation derived from boiling, or even just homogenising fruit in an aqueous solution. Fruit solids may be pelleted by centrifuging and the supernatant (containing soluble fibre) may be used according to the invention.

Clinical needs may dictate that such a crude preparation (re the supernatant mentioned above) may need to be used substantially "neat" or even diluted. When this is the case the supernatant (whether diluted or not) may be mixed with a number of other agents that may be added for nutritional reasons, medical reasons or even for the purposes of adjusting the palatability of the soluble fibres for consumption by the subject being treated.

For instance, the soluble fibre may be formulated with a diary product (e.g. milk, a milk shake or yoghurt) or a fruit juice (e.g. orange juice or similar) to produce a palatable drink/beverage with the added benefit that it contains soluble fibre and therefore will be highly suitable as a refreshment for sufferers of IBD.

Alternatively, the crude preparation may be included in a nutritional liquid for enteral feeding. For instance, the supernatant may be mixed with saline or an aqueous solution (other vitamins, minerals and nutrients may be included) for enteral feeding of subjects.

It will be appreciated that concentration of the crude preparation from the first protocol may be required or alternatively a powder composition is desired. When this is the case the crude extract/supernatant will need to be concentrated/dehydrated.

Compositions comprising soluble fibre may be formulated as powders, granules or semisolids for incorporation into capsules. For presentation in the form of a semisolid, soluble fibre can be dissolved or suspended in a viscous liquid or semisolid vehicle such as a polyethylene glycol, or a liquid carrier such as a glycol, e.g. propylene glycol, or glycerol or a vegetable or fish oil, for example an oil selected from olive oil, sunflower oil, safflower oil, evening primrose oil, soya oil, cold liver oil, herring oil, etc. This may then be filled into capsules of either the hard gelatine or soft gelatine type or made from hard or soft gelatine equivalents, soft gelatine or gelating-equivalent capsules being preferred for viscous liquid or semisolid fillings.

Powders comprising soluble fibre according to the invention are particularly useful for making pharmaceutical or nutritional products that may be used to prevent or treat IBD.

Freeze-drying or spray drying represent preferred methods for producing a powder comprising soluble fibres according to the invention. Spray drying results in free-flowing granular powder mixes with good flow properties and quick dissolving characteristics.

It will be appreciated that spray-dried or freeze-dried powder produced by the protocols discussed above represent preferred powdered soluble fibre according to the invention. A preferred powder is derived from a reconstituted soluble fibre solution produced by steps (i)–(v) (see above) which is subsequently freeze-dried or spray-dried.

Powdered soluble fibre may be reconstituted as a clear/translucent low viscosity drink/beverage. Reconstitution may be into water or dairy or fruit juices as discussed above. It will be appreciated that the powder may be packaged in a sachet and reconstituted as a drink by a subject when required or desired.

Powder mixes represent preferred embodiments of the invention. Such mixes comprise powdered soluble fibre (as described above) mixed with further ingredients. Such ingredients may be added for nutritional or medical reasons or for improved palatability. The powdered soluble fibre may be mixed with granulated sugars of varying particle sizes to obtain free-flowing powder mixes of varying sweetness.

Alternatively natural sweeteners or artificial sweeteners (e.g. aspartame, saccharin and the like) may be mixed with the powdered soluble fibre for reconstitution as a low calorie/reduced calorie sweetened drink. The powder mix may comprise a mineral supplement. The mineral may be any one of calcium, magnesium, potassium, zinc, sodium, iron, and their various combinations.

Powder mixes may also contain buffering agents such as citrate and phosphate buffers, and effervescent agents formed from carbonates, e.g. bicarbonates such as sodium or ammonium bicarbonate, and a solid acid, for example citric acid or an acid citrate salt.

The soluble fibre can be presented as food supplements or food additives, or can be incorporated into foods, for example functional foods or nutriceuticals. Such products may be used as staple foods as well as under circumstances where there may be a clinical need.

The powders may be incorporated in to snack food bars for example fruit bars, nut bars and cereal bars. For presentation in the form of snack food bars, the powder can be admixed with any one or more ingredients selected from dried fruits such as sundried tomatoes, raisins and sultanas, ground nuts or cereals such as oats and wheat.

It will be appreciated that soluble fibre may advantageously be formulated as a pharamaceutical for use as a medicament (requiring a prescription or otherwise).

Powdered soluble fibre or concentrated liquid soluble fibre may also be incorporated into tablets, lozenges, sweets or other food-stuffs for oral ingestion. It will also be appreciated that such powdered soluble fibre or concentrated liquid soluble fibre may be incorporated into slow-release capsules or devices which may be ingested and are able to release soluble fibre into the intestines over a long period of time.

Soluble fibres may also be microencapsulated. For instance encapsulation may be by calcium-alginate gel capsule formation. Kappa-carrageenan, gellan gum, gelatin and starch may be used as excipients for micro-encapsulation.

Crude preparations, liquid concentrates, powders and the like may be combined with known therapeutic agents for treating IBD. As such the soluble fibre according to the invention may be used in a very effective combination therapy. It will be appreciated that the soluble fibre in solution may act as an ideal vehicle for other therapeutic agents for treating IBD.

The soluble fibre may also be included in combination/synbiotic therapies that include a probiotic portion. The bacteria contained within many probiotic mixtures do not possess adhesive properties so would not be affected by the inclusion of plantain soluble fibre.

The compositions of the invention can be presented in the form of unit dosage forms containing a defined concentration of soluble fibre. Such unit dosage forms can be selected so as to achieve a desired level of biological activity.

The amount of a soluble fibre required by a subject is determined by biological activity and bioavailability which in turn depends on the formulation, mode of administration, the physicochemical properties of the soluble fibres and whether the soluble fibre is being used as a monotherapy or in a combined therapy. Generally, a daily dose for a human adult should be between 0.1 g and 100 g of freeze-dried or spray-dried powder (however formulated), more preferably the daily dose is between 1 g and 30 g (e.g. about 5 g, 10 g, or 15 g as required).

A solid or semisolid dosage form of the present invention can contain up to about 100 mg of dried extract containing soluble fibre, for example up to about 800 mg.

The frequency of administration will also be influenced by the above mentioned factors and particularly the half-life and of the soluble fibres within the subject being treated. For instance, the half-life will be influenced by the health status of the subject, gut motility and other factors.

The soluble fibre is particularly useful when included in pharmaceutical formulation such as a tablet or a capsule. Such formulations may be required to be enterally-coated if bioavailabilty dictates this. Known procedures, such as those conventionally employed by the pharmaceutical industry (e.g. in vivo experimentation, clinical trials etc), may be used to establish specific formulations of pharmaceutical compositions and precise therapeutic regimes (such as daily doses of the compounds and the frequency of administration).

It will be appreciated that conventional "nutriceutical" procedures may be employed to create liquid drinks, powder mixes and food-stuffs comprising the soluble fibre.

Daily doses may be given as a single administration (e.g. a daily tablet for oral consumption or as a single liquid drink). Alternatively the soluble fibre used may require administration twice or more times during a day. As an example, a 100 ml orange drink containing 0.1–20 g of spray dried soluble fibre (preferably 0.3–10 g of spray dried soluble fibre and more preferably 0.5–3.0 g) may be used to quench thirst at regular intervals throughout the day and thereby deliver a recommended dose.

It will be appreciated that nutritional products supplemented with soluble fibre represent an ideal means for providing subjects with, or at risk of developing, IBD with soluble fibre according to the present invention. Therefore, according to a fourth aspect of the present invention there is provided a nutritional product for use in the prevention or treatment of Inflammatory Bowel Disease comprising a therapeutically effective amount of a soluble fibre derivable from fruit of the *Musa* spp.

The nutritional product may comprise:
(a) a clear, low viscosity, water-like, stable, ready-to-use, bottled, carbonated or non-carbonated drink; or a concentrated clear liquid for reconstitution containing a non-gelling soluble fibre derivable from fruit of the *Musa* spp;
(b) a powder/granular mix to be reconstituted with water or any other orally ingestible liquid as a drinkable liquid, containing a non-gelling soluble fibre derivable from fruit of the *Musa* spp; or
(c) a powder/granular mix mixed into a food stuff (e.g. a chocolate bar, lozenge or the like).

The nutritional product may be as described above and may or may not contain water soluble vitamins, additional mineral supplements, nutritional compounds, antioxidants or flavourings.

The present invention will be further illustrated, by way of examples, with reference to the accompanying drawings in which.

EXAMPLE 1

The inventors conducted studies with the purpose of investigating IBD biopsies for the presence of bacterial populations which were either within the mucus layer; closely associated with the mucosa; or those which had invaded the mucosal layer. Cultured bacteria were fully characterised and those identified as *E. coli* were studied for their ability to adhere to human red blood cells. Adherent *E. coli* were further characterised for the presence of pathogenicity genes and known adhesins, their binding specificities and their ability to invade human intestinal cell lines.

1.1 Materials and Methods 1.1.1 Patients 60 patients were studied. 18 with ulcerative colitis, 14 with Crohn's disease and 28 normal controls. Biopsies were taken during colonoscopy or sigmoidoscopy for the majority of patients, one set of biopsies was taken from a resection sample from a normal patient with chronic inertia.

1.1.2 Bacterial Culture

Four biopsies were taken either from resected tissue samples (one patient) or at colonoscopy (59 patients). Biopsies were placed in 10 mls of physiological saline and transported on ice to the laboratory. The biopsies were placed in a 1.5 ml eppendorf containing 500 µl of 0.016% dithiothreitol (DTT) solution for 15 minutes to remove the mucus layer. 50 µl of DTT supernatant was plated onto MacConkey agar and incubated at 37° C. for 24 hrs. The biopsies were then separated into two 1.5 ml eppendorfs containing either 500 µl sterile saline or 500 µl gentamicin (50 ml/L). After 30 mins the biopsies were washed 4 times by transferring them into consecutive 1.5 ml eppendorfs containing 500 µl saline. After the fourth wash, one biopsy from each eppendorf (i.e one of the gentamicin-treated biopsies and one of the non-gentamicin-treated biopsies) was placed into sterile distilled and de-ionised water, the other biopsy from each eppendorf was placed in 500 µl saline. After a further 30 mins, 50 µl solution from each of the final eppendorfs were plated onto MacConkey agar plates. After 24 hrs incubation at 37° C., colony counts were performed.

1.1.3 Bacterial Identification

After the colony counts had been performed the bacterial colonies were characterised and 5 of each colony type were subcultured onto nutrient agar. Gram staining was performed and any bacteria identified as Gram negative rods were further identified using API20E bacterial identification kits (BioMerieux, Fr). Bacterial samples from each subcultured colony were stored on Protect beads at −80° C.

1.1.4 Antibiotic Resistance Assay

A single well isolated bacterial colony was suspended in 5 mls of sterile saline using colonies of bacteria taken from a nutrient agar plate. 100 µl of the bacterial suspension was plated onto sensitivity agar plates. Antibiotic discs were then dispensed onto the plate. The following antibiotics were used: Gentamicin, Trimethoprim, Sulphonomide, Ampicillin, Penicillin, Tetracycline, Naladixic acid, Chloramphenicol. The bacterial plates were incubated at 37° C. overnight. The diameters of bacterial growth around the discs were measured and the degree of bacterial resistance to the antibiotics was calculated.

1.1.5 Bacterial Growth Conditions for Maximum Fimbrial Expression

Figure 1:
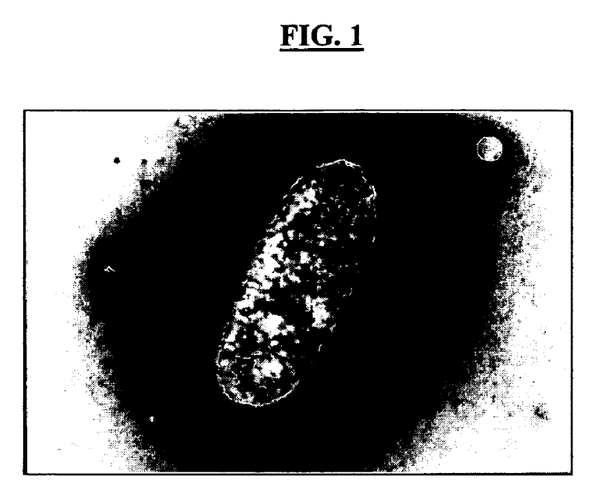
FIG. 1 illustrates fimbrial expression by a mucosa-associated *E. coli* using electron microscopy (some indicated by arrows) in Example 1.

Maximum fimbrial expression was seen after bacterial colonies grown overnight on nutrient agar, suspended in sterile saline, and then left at room temperature for 48 hrs. Fimbrial expression was confirmed using EM and may be seem in FIG. 1.

1.1.6 Haemagglutination Assays

Blood was taken from a healthy human volunteer and placed into a heparinised container. The blood was washed three times in PBS by centrifugation at 1000 rpm for 5 minutes and by resuspending the pellet in fresh PBS. After the third wash, the pellet was resuspended in PBS so as to give a 1% red blood cell solution. Bacteria identified as *E. coli*, and 5 strains of CD-ileal associated *E. coli* were grown so as to obtain maximum fimbrial expression (see above). Bacteria were suspended in saline to give an OD equal to MacFarland standard 5. Doubling dilutions of bacterial suspension were performed in 96 well U-bottomed haemagglutination plates (Dynex technologies) to a final volume of 100 µl per well. 50 µl of 1% rbcs was added to each well. The plate was tapped gently to mix the contents of the wells and was left at room temperature for approximately 2 hrs.

1.1.7 Haemagglutination Assays Using the Human rbc Panel

All *E. coli* were tested against a panel of rbcs of known antigenic type. These included ID panel 1 (26 antigens including Lewis, Lutheran, M, N, S, P, K, Kidd, Rhesus and others), A1rr cells, Brr cells (ABO blood groups) (NBS reagents, Liverpool, UK) and adult ii cells (Diagnostics Scotland, Edinburgh, UK).

1.1.8 Haemagglutination Assays with Different Oligosaccharides/Fibres

Further characterisation of bacterial haemagglutination was carried out using a panel of oligosaccharides/fibres. The structures tested were: mannose (0.4M), fucose (0.4M), galactose (0.4M), fetuin (50 µg/ml), asialofetuin (50 µg/ml), bovine submaxillary mucin (BSM), hydrolysed BSM, ovine submaxilliary mucin (OSM), lactose, lactulose, siayl Tn, GalGalNAc, N-Glycolyneuraminic acid, N-acetyineuraminic acid, 3'-n-acetylneuraminyl-lactose, 6'-n-acetylneuraminyl-lactose, melibiose, plantain, stachyose, milk derived galacto-oligosaccharide, raffinose, pectin, polygalacturonic acid, and paralacto-n-hexaose.

1.1.9 PCR

Bacteria identified as agglutinating *E. coli* were screened both for pathogenicity genes associated with virulent strains of *E. coli* and for known adhesin genes. These were: VT1, VT2, VT2e, STI, STII, LTI, Einv, Eagg, CNF1, CNF11, EaeA, EaeB, EAF, Bfp, CDT, EAST, Hly, HlyA, pap, sfa, afa, M-agglutinin, fimH.

1.1.10 Pulse Field Gel Electrophoresis

Agglutinating strains of *E. coli* were tested for clonality using Pulse field gel electrophoresis.

1.1.11 Attachment and Invasion Assays

Agglutinating bacteria were tested for their ability to adhere to and invade the intestinal cell lines I-407 and HT-29. *Shigella sonni* was used as a positive control for invasion and *E. coli* K12, an adherent but non-invasive *E. coli*, was used as a negative control for invasion. Cells were maintained in DMEM (Dulbecco's modified eagles medium—Sigma, UK) at 37° C., 5% $CO_2$, supplemented with 10% (vol/vol) heat inactivated fetal calf serum (Sigma, UK), 1% L-glutamine, penicillin and streptomycin. Monolayers were seeded into 24-well tissue culture plates (Costar, UK), with $4 \times 10^5$ cells/well. Cells were incubated for 20 hrs. The monolayers were washed twice with phosphate buffered saline (PBS). Bacteria were grown so as to maximise fimbrial expression (48 hrs in saline). Each monolayer was infected with approximately $7 \times 10^6$ bacteria/well in culture medium without antibiotic. After 3 hrs incubation at 37° C., the monolayers were washed three times with PBS. To determine bacterial invasion, wells were treated with fresh culture medium containing gentamicin (100 µg/ml), the purpose of this is to kill any extracellular bacteria as gentamicin cannot penetrate human cells. After one hour at 37° C., the monolayers were washed three times in sterile PBS. Monolayers were lysed by adding deionised water containing 1% Triton X-100 for 5 minutes. Ten-fold dilutions of the cell lysate were performed and 50 µl was plated onto nutrient agar plates. Plates were incubated at 37° C. and colony forming units (CFUs) were counted after 24 hrs. Bacterial attachment was calculated as total CFU counts multiplied by the dilution factor, this has also been expressed as a percentage of the total number of bacteria used to inoculate the wells. Bacterial invasion was defined as the percentage of the attached bacteria which survived gentamicin treatment. A time course of bacterial attachment and invasion was determined using only I-407 cells over a period of 5 hrs.

1.1.12 Effect of Plantain Soluble Fibre on Attachment and Invasion of Bacteria

The effect of pre-incubating bacteria with plantain on attachment and invasion of *E. coli* was studied.

1.1.12.1 Preparation of freeze-dried plantain soluble fibre: skins were removed from plantains and the whole fruit (excluding skins) freeze-dried and then milled. It was then boiled (100° C.) for approximately 30 mins in water to gelatinise the starch and disperse any starch granules. It was then hydrolysed with porcine pancreatic amylase (at 40° C.) to ensure all the starch was removed. The Non-Starch Polysaccharides (NSP) fraction was precipitated and washed with 80% ethanol and centrifuged (about 10,000 g). The alcoholic supernatant was then discarded and the residue (containing both soluble and insoluble NSP) was freeze-dried. This freeze-dried sample represents a powdered soluble fibre according to the invention.

1.1.12.2 Preparation of plantain soluble fibre solution: When a sample of soluble fibre was required the freeze-dried residue (1.1.12.1) was boiled in water for 30 mins, centrifuged at 10,000 g for 10 mins and the supernatant taken as the soluble fibre of plantain.

1.1.12.3 Preparation of refined freeze-dried plantain soluble fibre: the supernatant (1.1.1.2.2) was freeze-dried (as described above) to form a preferred powdered soluble fibre according to the invention.

1.1.13 Preparation of Bacteria for Use in Attachment and Invasion Assays.

1 ml of the bacterial cultures, which had been grown in sterile saline to achieve maximum fimbrial expression, were pipetted into two eppendorfs. The tubes were centrifuged at 10 000 g for 5 minutes. The supernatant was discarded and the pellet from one tube was resuspended in 1 ml of soluble plantain solution. The other pellet was resuspended in 1 ml sterile saline. Both eppendorfs were rotated in the cell-spinner for 30 mins. The bacterial suspensions were centrifuged as before and the pellets were washed twice in sterile saline. The pellets were finally resuspended in 1 ml of sterile saline and were used in the attachment and invasion assay as before.

1.2 Results

1.2.1 Increased Mucosally-Associated Bacteria in Crohn's Disease

Bacteria were identified using the microbiological techniques described in the Methods section.

In total, of 707 bacterial colonies sub-cultured, 406 were Gram negative and 292 of these were identified as *E. coli*. Sensitivity to antibiotics such as gentamicin, trimethoprim, sulphonomide, ampicillin, penicillin, tetracycline, naladixic acid and chloramphenicol was examined to further characterise the bacteria (data not shown).

Figure 2:
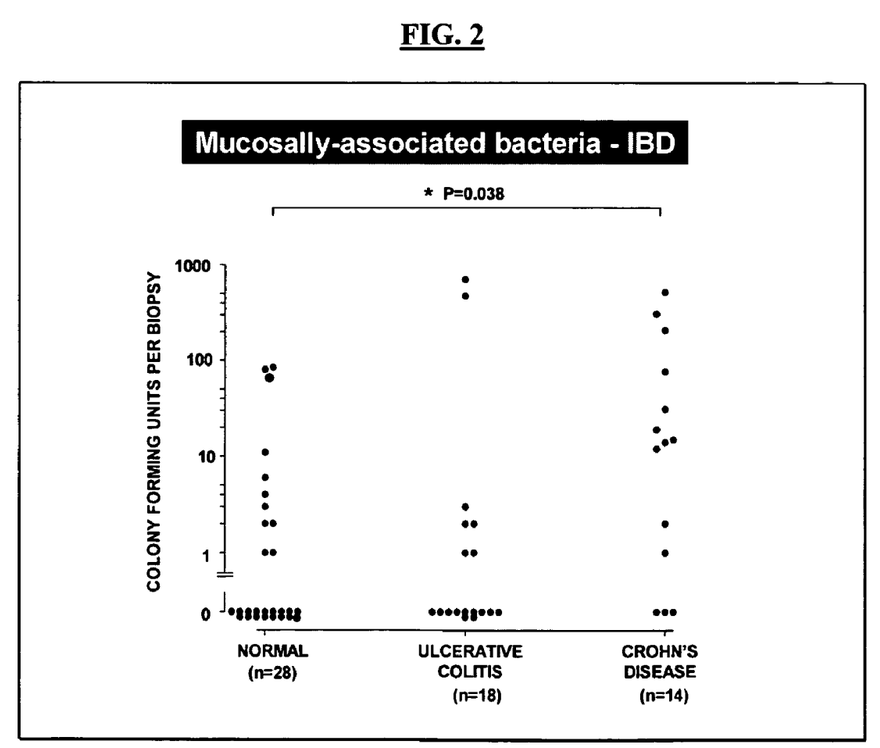
FIG. 2 is a graph showing a significant increase in mucosally-associated bacteria in patients with Crohn's disease in Example 1.

Mucus-associated bacteria were cultured from the supernatent of dithiothreitol (DTT)-treated biopsies (DTT removes the mucus layer from the biopsy exposing the mucosa). No significant difference in numbers of mucus-associated bacteria was found between patient groups (data not shown). However FIG. 2 shows a significant increase in mucosally-associated bacteria in patients with Crohn's disease compared to control patients with 79% (11/14) of CD patients being positive for mucosally-associated bacteria compared to 39% (11/28) of control patients (P=0.038; Chi-square). Mucosally-associated bacteria are those that can be recovered from the mucosal surface after surface mucus has been removed by DTT treatment and extensive washing.

This data indicate, as suspected by the inventors, that there is an increase in mucosally-associated bacteria in IBD.

1.2.2 Mucosally-Associated *E. coli* Express Haemagglutinins

Figure 3:
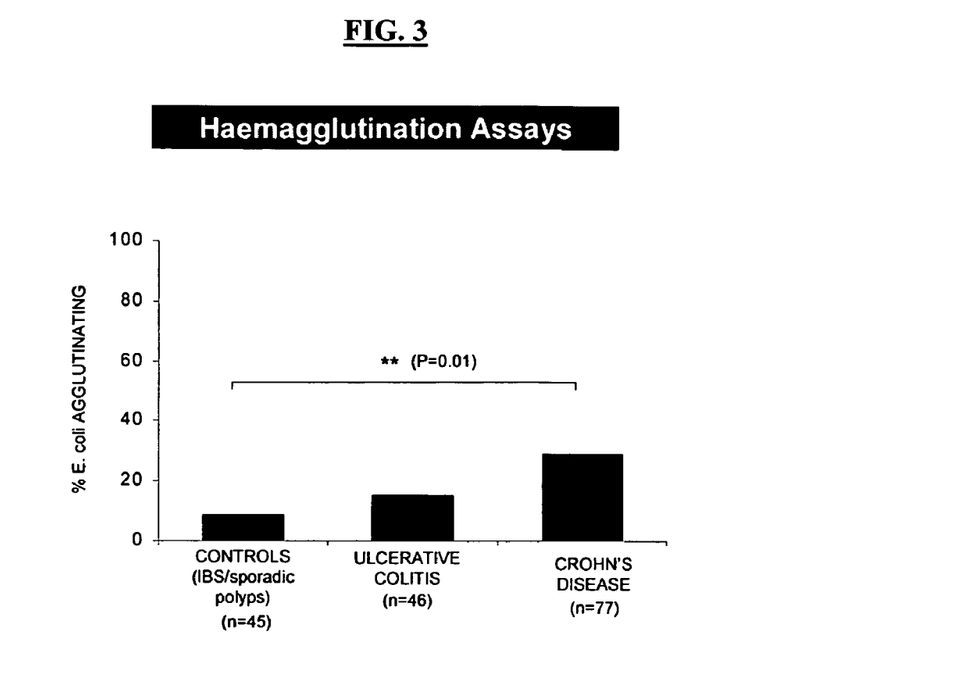
FIG. 3 shows that significantly more *E. coli* isolated from Crohn's disease tissue possessed heamagglutinating activity as compared to *E. coli* isolated from control patients in Example 1.

FIG. 3 illustrates that significantly more *E. coli* isolated from Crohn's disease tissue possessed haemagglutinating activity as compared to *E. coli* isolated from control patients. Haemagglutinating *E. coli* were identified in 39% (5/14) of CD patients compared to 4% (1/28) of controls (P=0.01). An increased number of bacteria from UC patients was also able to agglutinate.

It was also found that bacteria capable of agglutinating red blood corpuscles (rbcs) from a healthy human volunteer, were also able to agglutinate rbcs from a panel of rbcs of known antigenic type supplied by the blood transfusion centre. Crohn's disease-associated strains of *E. coli* were also shown to have selective binding to the rbc panel. The binding pattern of this *E. coli* suggested that it possessed a blood group 'M'-specific adhesin. This bacterium was further characterised using PCR.

These data suggest that mucosally associated *E coli* interact with intestinal cells by means of interaction with glycosylated proteins on the cell surface. This further confirmed the inventors hypothesis relating to the mechanism by which bacteria invade the intestine in IBD.

1.23. Mucosally-Associated *E coli* Adhere to and Invade Intestinal Cells in Culture 16 different strains of agglutinating *E. coli* were characterised according to methods 1.1.4, 1.1.9 and 1.1.10 and subjected to attachment and invasion assays according to method 1.1.11. The human colonic cell-line, HT29 and the human intestinal cell line, I-407 were used in the experiments.

All agglutinating *E. coli* were shown to adhere to both HT29 and I407 cell-lines, but invasion in the main, was seen only in I407 cells (see Table 2). Invasion and adherence were calculated by using the mean number of colony forming units (CFU's) recovered from non-gentamicin and gentamicin-treated cells (n=4). (Gentamicin kills all non-invading *E coli* but cannot penetrate the intestinal cells so leaves bacteria that have invaded intact). LF82 is an adherent and invasive *E. coli* (AIEC) isolated from an ileal Crohn's disease lesion. *Shigella sonnei* was used as a positive control for invasion, and *E. coli* K12 was used as a negative control for invasion. It is known to adhere to cells via a mannose-binding adhesin but is non-invasive.

Figure 4:
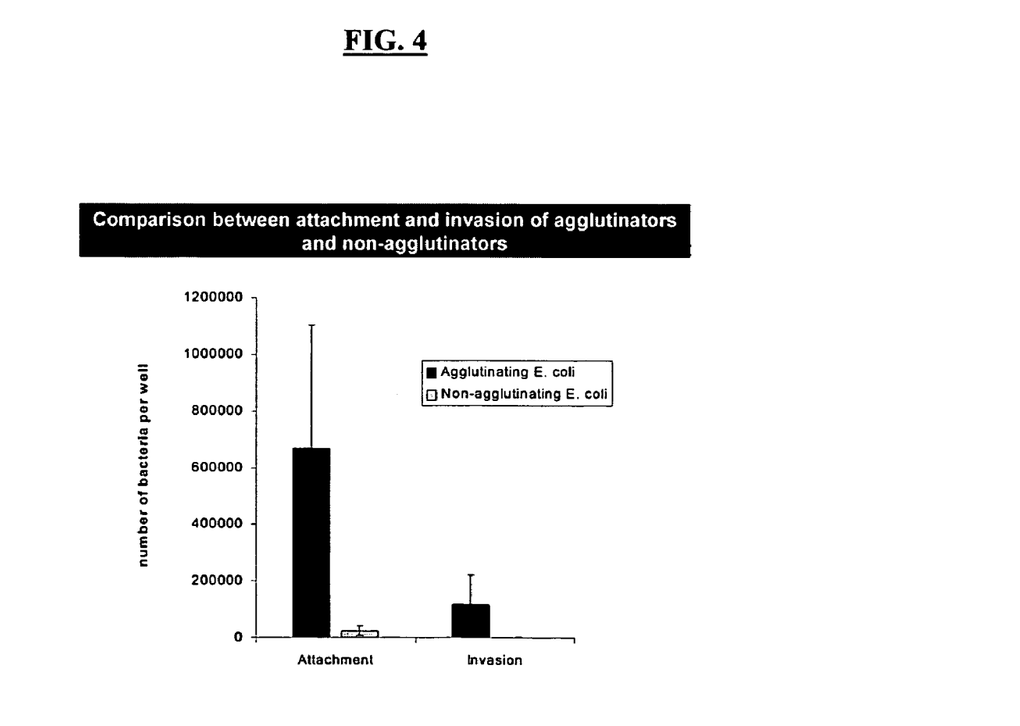
FIG. 4 shows that agglutinating strains of *E. coli* are able to attach to and invade I-407 cells at a significantly higher level than non-agglutinating strains of *E. coli* (this validates the use of the haemagglutination assay to assess inhibition of bacterial adhesion)

Further experiments were performed to compare agglutinating *E. coli* (such as those from subjects with IBD) with non-agglutinating *E. coli*. in respect of their ability to attach and invade I-407 cells. FIG. 4 illustrates a correlation between the ability of a bacterium to agglutinate and adhere to intestinal cells. This therefore further suggests that bacteria in IBD invade the mucosa by a targeting mechanism involving glycoproteins.

TABLE 3

Invasion and adherence of agglutinating bacteria

| Haemagglutinating *E. coli* strain (except *) | Original inoculum (bacteria ×10⁶/well) | N° BACTERIA ATTACHED (×10⁴/well) | | % INVASION | |
|---|---|---|---|---|---|
| | | I-407 CELLS | HT-29 CELLS | I-407 CELLS | HT-29 CELLS |
| 1 | 2.20 | 1.27 ± 0.83 | 0.05 ± 0.1 | 14.62 ± 18.89 | 0.00 |
| 2 | 10.40 | 5.56 ± 3.25 | 0.33 ± 0.19 | 0.99 ± 2.99 | 0.00 |
| 3 | 7.60 | 7.23 ± 3.99 | 0.025 ± 0.05 | 4.23 ± 6.54 | 0.00 |
| 4 | 22.00 | 2.49 ± 1.32 | 0.58 ± 0.27 | 1.00 ± 2.87 | 0.00 |
| 5 | 3.80 | 35.4 ± 14.14 | 28.00 ± 0.57 | 0.23 ± 0.74 | 0.00 |
| 6 | 7.00 | 0.34 ± 0.36 | 0.16 ± 0.19 | 0.00 | 0.00 |
| 7 | 1.20 | 1.18 ± 11.79 | 0.01 ± 0.02 | 2.98 ± 3.50 | 0.00 |
| 8 | 1.80 | 29.70 ± 11.74 | 3.00 ± 1.95 | 0.03 ± 0.10 | 0.17 ± 0.51 |
| 9 | 3.60 | 78.40 ± 4.53 | 4.73 ± 0.71 | 0.31 ± 1.49 | 0.11 ± 1.42 |
| 10 | 8.80 | 4.82 ± 1.62 | 0.31 ± 0.25 | 1.77 ± 5.75 | 0.00 |

TABLE 3-continued

Invasion and adherence of agglutinating bacteria

| Haemagglutinating E. coli strain (except *) | Original inoculum (bacteria ×10$^6$/well) | N° BACTERIA ATTACHED (×10$^4$/well) | | % INVASION | |
|---|---|---|---|---|---|
| | | I-407 CELLS | HT-29 CELLS | I-407 CELLS | HT-29 CELLS |
| 11 | 15.00 | 2.51 ± 1.32 | 0.03 ± 0.04 | 6.79 ± 9.05 | 0.00 |
| 12 | 2.40 | 11.30 ± 2.69 | 0.31 ± 0.23 | 9.87 ± 21.71 | 0.00 |
| 13 | 6.60 | 27.60 ± 10.75 | 3.54 ± 0.70 | 0.65 ± 1.50 | 1.98 ± 13.57 |
| 14 | 21.80 | 15.00 ± 3.11 | 0.25 ± 0.27 | 10.9 ± 6.61 | 0.00 |
| 15 | 2.20 | 0.29 ± 0.22 | 0.44 ± 0.57 | 0.00 | 0.00 |
| 16 | 4.80 | 3.04 ± 1.82 | 0.47 ± 0.28 | 2.30 ± 4.96 | 0.00 |
| LF10 | 9.00 | 56.30 ± 3.25 | 61.20 ± 12.16 | 0.82 ± 7.22 | 0.00 |
| LF82 | 11.60 | 2.06 ± 0.94 | 0.45 ± 0.33 | 12.90 ± 38.99 | 12.36 ± 29.87 |
| K12 | 9.40 | 9.80 ± 3.11 | 0.40 ± 0.25 | 0.00 | 0.00 |
| * Shigella sonnei | 4.00 | 2.34 ± 1.91 | 3.64 ± 1.13 | 40.38 ± 30.43 | 3.99 ± 15.57 |

1.2.4 The Effect of Soluble Fibre on Bacteria Isolated from Subjects with IBD

Soluble fibre (prepared according to 1.1.12.2) and other carbohydrates were tested for their ability to modulate agglutination, attachment and invasion of cells from subjects with IBD.

1.2.4.1 Agglutination: In all cases agglutination was inhibited by soluble plantain fibre and bovine submaxillary mucin (BSM) but not following mild acid hydrolysis of BSM to remove sialic acid and fucose.

A range of other carbohydrates and glycoconjugates, including mannose, fucose, galactose, lactose, lactulose, siaylosyl-Tn, Galβ1–3GalNAc, N-glycolyneuraminic acid, N-acetyineuraminic acid, 3'-n-acetylneuraminyl-lactose, 6'-n-acetylneuraminyl-lactose, melibiose, stachyose, milk derived galacto-oligosaccharide, raffinose, polygalacturonic acid, and paralacto-n-hexaose, fetuin, asialofetuin, ovine submaxilliary mucin and pectin were non-inhibitory.

1.2.4.2 Inhibition of bacterial attachment by plantain soluble fibre: Bacterial strains 9, 12 and 14 (as identified in Table 3) were FIG. 4 illustrates that plantain soluble fibre significantly reduced bacterial attachment of bacterial strains 9 and 12 to I-407 cells. No significant difference can be seen for strain 14 although limited attached was seen for this strain in the presence or absence of soluble fibre.

Figure 5:
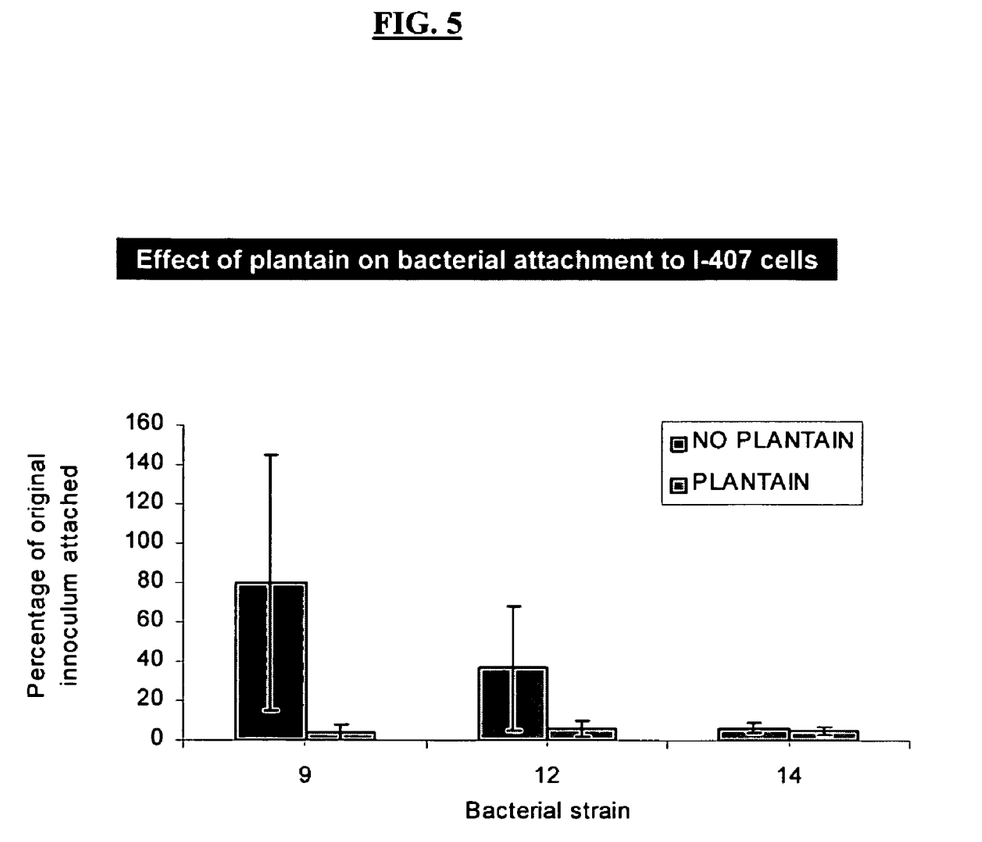
FIG. 5 is a graph illustrating that plantain soluble fibre significantly reduced bacterial attachment to cells in Example 1.
Figure 6:
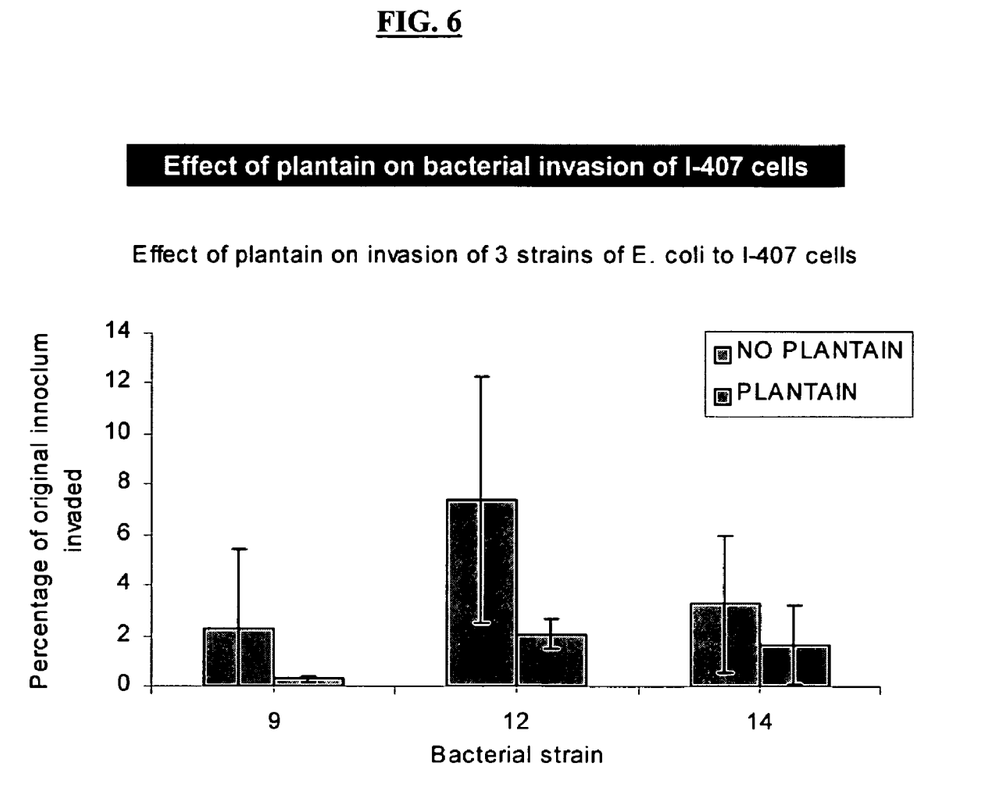
FIG. 6 is a graph illustrating that plantain soluble fibre significantly reduced bacterial invasion to cells in Example 1.

1.2.4.3 Inhibition of bacterial invasion by plantain: FIG. 5 illustrates that bacterial invasion is reduced by pre-incubation of each of three bacterial strains (strains 9, 12 and 14 from Table 2) with plantain soluble fibre.

1.3 Discussion

These data demonstrate that IBD such as Crohn's disease is associated with an increased prevalence of mucosally-associated E. coli. These E. coli lacked known pathogenicity genes but include a high proportion which express haemagglutinins which allow them to adhere to, and invade, intestinal epithelial cell lines. The inventors believe that the adhesive and invasive nature of the bacterium cause an inflammatory condition and thereby characterise IBD.

The inventors established a link between IBD and the ability of bacteria from subjects with IBD to agglutinate. They therefore reasoned that binding of bacteria in IBD must be regulated by carbohydrates and tested many oligosaccharides to evaluate whether or not they would inhibit the negative effects of E. coli in IBD. Most of the sugars/oliogosaccharides tested failed to modulate the bacteria. However, surprisingly, soluble fibre from plantain inhibited E. coli. This led the inventors to realise that soluble fibre according to the invention comprises bacteria modifying oligosaccharides for therapeutic use in IBD such as Crohn's disease.

It will be appreciated that these data suggest that soluble fibre according to the invention will also be useful for treating or preventing the development of other gastrointestinal conditions which may be characterised by bacterial adhesion and invasion (e.g. colon cancer, diarrhoeal disease/infections, gastroenteritis or Type 1 Glycogen-storage disease.

EXAMPLE 2

Production of a Powder of Plantain Soluble Fibre for Use According to the Invention 250 g of chopped plantain pulp was dropped into 1,000 ml of boiling and then treated as described in 1.1.12.1 The freeze-dried yield of Soluble Fibre (1.1.12.2) was approximately 4.0 g

EXAMPLE 3

Production of a Powder Mix of Plantain Soluble Fibre for Use According to the Invention 3.0 g of freeze dried soluble fibre powder (Example 2) was mixed with 0.5 g powdered citric acid, 26.3 g of granulated sugar and 0.2 g of a standard spray-dried mix of flavouring.

This mixture represents a free-flowing powder formulation (containing 3.0 g of soluble fibre) that is suitable for packaging in a sachet. The powder mix may be diluted to taste and drunk when required by a subject suffering from IBD.

EXAMPLE 4

Production of an Alternate Powder Mix of Plantain Soluble Fibre for Use According to the Invention 3.0 g of spray-dried soluble fibre powder (Example 1.1.12.1) was mixed with 0.5 g powdered citric acid, 26.3 g of granulated sugar and 0.2 g of a standard spray-dried mix of flavouring.

This mixture represents a free-flowing powder formulation (containing 3.0 g of soluble fibre) that is suitable for packaging in a sachet. The powder mix may be diluted to taste and drunk when required by a subject suffering from IBD.

EXAMPLE 5

Production of an Orange Drink for Use According to the Invention (a) 100 ml of crude preparation (prepared according to method 1.1.12.2) was mixed with 100 mls of double concentrate orange juice (orange juice concentrate diluted in water to double strength).

(b) 3.5 g of freeze-dried powder (prepared according to the method 1.1.12.1) was dissolved in 100 mls of orange juice (or alternatively with orange juice concentrate and water).

(c) 2.5 g of freeze-dried powder (prepared according to the method 1.1.12.3) was dissolved in 100 mls of orange juice (or alternatively with orange juice concentrate and water).

The orange drink preparations (a, b or c) may be consumed by a subject immediately, refrigerated for later consumption or sealed in a bottle or carton for a longer shelf life.

It will be appreciated that orange juice may be readily substituted with a palatable alternative.

EXAMPLE 6

Production of a Nutritional Liquid Formulation Containing Plantain Soluble Fibre for Use in Enteral Feeding A liquid nutritional mixture may be produced for use in enteral feeding in which the total content of the NSP (method as in Example 1.1.12.1) is between 0.1 and 10% of the total dry matter content of the feed mixture. The NSP may be mixed with saline or an aqueous solution, and other vitamins, minerals and nutrients may be included as required for enteral feeding of subjects. Such enteral liquid formulations may be packaged in pouches (e.g containing 100 mls–2,000 mls) for use in a drip or for insertion into a pump feed.

EXAMPLE 7

Further experiments (following the protocols described in Example 1) were conducted to test the efficacy of soluble fibre according to the invention that had been prepared by homogenising/extracting the fibre at pH7 (column 3 of Table 4); heating the solution to either 40° C. or 100° C. (column 4 of Table 4); treating the heated solution to remove starch (column 5 of Table 4); isolating the soluble fibre (column 3 of Table 4).

TABLE 4

| Tube No | Sample 2 grams | Extraction pH | Extraction Temp | Enzyme Treatment (1 h) | Ethanolic Precipitation (Supernatant discarded) | Agglutinin titre (6 = + at 1/64 ediln) |
|---|---|---|---|---|---|---|
| A | HM 233 (UCisolate) | | | | | 6 |
| 1 | Plantain flesh | 7 | 40° C. | Nil | 80% | 4 |
| 2 | Plantain flesh | 7 | 40° C. | Termamyl | 80% | 0 |
| 3 | Plantain flesh | 7 | 40° C. | Nil | Nil | 0 |
| 4 | Plantain flesh | 7 | 100° C. | Pancreatin | 80% | 0 |
| 5 | Plantain flesh | 7 | 100° C. | Pancreatin | Nil | 1 |
| 6 | Plantain flesh | 7 | 100° C. | Termamyl | 80% | 0 |
| 7 | Plantain flesh | 7 | 100° C. | Termamyl | Nil | 0 |
| 8 | Crude banana | N/A | | Nil | Nil | 0 |
| 9 | Crude plantain | N/A | | Nil | Nil | 2 |

| Tube No | Sample | pH | Temp | Enzyme Treatment | Ethanolic Precipitation | Agglutinin titre |
|---|---|---|---|---|---|---|
| A | Control Bug (233: UC) | | | | | 6 |
| 5B | Blank | 7 | 100° C. | Pancreatin | 80% | 5 |
| 6B | Blank | 7 | 100° C. | Pancreatin | Nil | 5 |
| 7B | Blank | 7 | 100° C. | Termamyl | 80% | 5.5 |
| 8B | Blank | 7 | 100° C. | Termamyl | Nil | 6 |

The final volume is approximately 10 ml corresponding to 200 mg plantain flesh per ml.

The data illustrated in Table 4 demonstrates that soluble fibre derived from plantain and prepared as described herein (i.e. Tubes 1–7) had efficacy for reducing bacterial agglutination. This effect is indicative to a skilled person that the soluble fibre is useful for the prevention or treatment of inflammatory bowel disease. Tubes 8 & 9 were positive control whereas tubes A and 5B–8D represent negative controls.

The invention claimed is:

1. A method for treating Inflammatory Bowel Disease in a subject with inflammatory bowel disease, comprising:
   providing a composition comprising a substantially starch free soluble fibre derived from a plantain; and
   administering a therapeutically effective amount of the composition to the subject with Inflammatory Bowel Disease,
   whereby the Inflammatory Bowel Disease is treated.

2. The method of claim 1, wherein the soluble fibre is derived from an aqueous solution decanted from homogenised plantain.

3. The method of claim 1, wherein the soluble fibre is derived from the precipitate of an aqueous solution, comprising a plantain, treated with ethanol.

4. The method of claim 3, wherein the soluble fibre is derived from a precipitate of the aqueous solution subjected to a precipitation step with 80% ethanol.

5. The method of claim 1, wherein the composition is in powder form.

6. The method of claim 1, wherein the composition further comprises at least one flavouring, at least one sugar, at least one sweetener, at least one anti-oxidant, at least one mineral, at least one vitamin, or a combination thereof.

7. The method of claim 1, wherein the Inflammatory Bowel Disease is Crohn's Disease.

8. The method of claim 1, wherein the composition further comprises a pharmaceutically acceptable carrier.

9. The method of claim 1, wherein the composition is a liquid, a capsule, or a tablet for oral consumption.

10. A composition for use in the treatment of Inflammatory Bowel Disease, comprising a therapeutically effective amount of a substantially starch free soluble fibre derived from fruit of the *Musa* spp. obtained by:
    (1) chopping fresh fruit of the *Musa* spp. and removing any skins therefrom and placing the chopped fruit in an aqueous solution; or freeze-drying skinned whole fruit of the *Musa* spp., milling the dried fruit and placing the milled dried fruit in an aqueous solution; or milling desicated fruit of the *Musa* spp. and placing the milled desicated fruit in an aqueous solution; or providing flour prepared from fruit of the *Musa* spp. and placing the flour in an aqueous solution;
    (2) taking the solution from (1) and heating to gelatinise starch and disperse any starch granules;
    (3) cooling the heated solution from (2) and hydrolysing with starch digesting enzymes to ensure that all or most of the starch is removed;
    (4) taking the solution from (3) and precipitating and washing with 80% ethanol;
    (5) centrifuging the solution from (4); and
    (6) discarding the ethanolic supernatant and freeze-drying or spray-drying the residue.

11. The composition according to claim 10, wherein heating the solution comprises boiling the solution.

12. The composition according to claim 10 in powder form.

13. The composition according to claim 10, further comprising at least one flavouring, sugar, sweetener, anti-oxidant, mineral or vitamin.

14. The composition according to claim 10, wherein the Inflammatory Bowel Disease is Crohn's Disease.

15. A composition for use in the treatment of Inflammatory Bowel Disease, comprising a therapeutically effective amount of a substantially starch free soluble fibre derived from fruit of the *Musa* spp. obtained by:
    (a) freeze-drying and milling skinned whole fruit of the *Musa* spp.;
    (b) boiling the milled material to gelatinise any starch and disperse any starch granules;
    (c) hydrolysing starch in the material with amylase;
    (d) precipitating and washing the material with ethanol and freeze drying or spray drying to produce a residue; and
    (e) reconstituting the freeze-dried or spray-dried residue, boiling the reconstituted residue and centrifuging the reconstituted and boiled residue,
    wherein the supernatant from the centrifugation (e) comprises the substantially starch free soluble fibre.

16. The composition according to claim 15, wherein the composition is in powder form, and the powder comprises the supernatant of step (e) that is spray-dried or freeze-dried.

17. A nutritional product for use in the treatment of Inflammatory Bowel Disease comprising a therapeutically effective amount of a substantially starch free soluble fibre derived from fruit of the *Musa* spp. obtained by:
    (1) chopping fresh fruit of the *Musa* spp. and removing any skins therefrom and placing the chopped fruit in an aqueous solution, or freeze-drying skinned whole fruit of the *Musa* spp., milling the dried fruit and placing the milled dried fruit in an aqueous solution, or milling desicated fruit of the *Musa* spp. and placing the milled desicated fruit in an aqueous solution, or providing flour prepared from fruit of the *Musa* spp. and placing the flour in an aqueous solution,
    (2) taking the solution from (1) and heating to gelatinise starch and disperse any starch granules,
    (3) cooling the heated solution from (2) and hydrolysing with starch digesting enzymes to ensure that all or most of the starch is removed,
    (4) taking the solution from (3) and precipitating and washing with 80% ethanol,
    (5) centrifuging the solution from (4), and
    (6) discarding the ethanolic supernatant and freeze-drying or spray-drying the residue; or
    (a) freeze-drying and milling skinned whole fruit of the *Musa* spp.,
    (b) boiling the milled material to gelatinise any starch and disperse any starch granules,
    (c) hydrolysing starch in the material with amylase,
    (d) precipitating and washing the material with ethanol and freeze drying or spray drying to produce a residue, and
    (e) reconstituting the freeze-dried or spray-dried residue, boiling the reconstituted residue and centrifuging the reconstituted and boiled residue,
    wherein the supernatant from the centrifugation (e) comprises the substantially starch free soluble fibre.

18. A nutritional product according to claim 17 in the form of a beverage or drink.

19. The nutritional product according to claim 18 comprising between 1 g/100 ml and 30 g/100 ml of the substantially starch free soluble fibre.

20. A nutritional product according to claim 17 in the form of a powder or powder mix.

21. A nutritional product according to claim 17 in the form of a food bar or other solid food stuff.

22. A method of producing a composition comprising a quantity of a substantially starch free soluble fibre derived from fruit of the *Musa* spp. for use in the treatment of Inflammatory Bowel Disease, the method comprising:
    (1) chopping fresh fruit of the *Musa* spp. and removing any skins therefrom and placing the chopped fruit in an aqueous solution; or freeze-drying skinned whole fruit of the *Musa* spp., milling the dried fruit and placing the milled dried fruit in an aqueous solution; or milling desicated fruit of the *Musa* spp. and placing the milled desicated fruit in an aqueous solution; or providing flour prepared from fruit of the *Musa* spp. and placing the flour in an aqueous solution'
    (2) taking the solution from (1) and heating to gelatinise starch and disperse any starch granules;
    (3) cooling the heated solution from (2) and hydrolysing with starch digesting enzymes to ensure that all or most of the starch is removed;
    (4) taking the solution from (3) and precipitating and washing with 80% ethanol;
    (5) centrifuging the solution from (4);

(6) discarding the ethanolic supernatant and freeze-drying or spray-drying the residue; and (7) adding a quantity of the residue to the composition.

23. A method of producing a composition comprising a quantity of a substantially starch free soluble fibre derived from fruit of the *Musa* spp. for use in the treatment of Inflammatory Bowel Disease, the method comprising:
   (a) freeze-drying and milling skinned whole fruit of the *Musa* spp.;
   (b) boiling the milled material to gelatinise any starch and disperse any starch granules;
   (c) hydrolysing starch in the material with amylase;
   (d) precipitating and washing the material with ethanol and freeze drying or spray drying to produce a residue;
   (e) reconstituting the freeze-dried or spray-dried residue, boiling the reconstituted residue and centrifuging the reconstituted and boiled residue, wherein the supernatant from the centrifugation (e) comprises the substantially starch free soluble fibre; and
   (f) adding a quantity of the supernatant to the composition.

24. A method for treating Inflammatory Bowel Disease in a subject, comprising:
   providing a composition comprising a substantially starch free soluble fibre derived from fruit of *Musa* spp. obtained by:
   (1) chopping fresh fruit of the *Musa* spp. and removing any skins therefrom and placing the chopped fruit in an aqueous solution, or freeze-drying skinned whole fruit of the *Musa* spp., milling the dried fruit and placing the milled dried fruit in an aqueous solution, or milling desicated fruit of the *Musa* spp. and placing the milled desiccated fruit in an aqueous solution, or providing flour prepared from fruit of the *Musa* spp. and placing the flour in an aqueous solution,
   (2) taking the solution from (1) and heating to gelatinise starch and disperse any starch granules,
   (3) cooling the heated solution from (2) and hydrolysing with starch digesting enzymes to ensure that all or most of the starch is removed,
   (4) taking the solution from (3) and precipitating and washing with 80% ethanol,
   (5) centrifuging the solution from (4), and
   (6) discarding the ethanolic supernatant and freeze-drying or spray-drying the residue; or
   (a) freeze-drying and milling skinned whole fruit of the *Musa* spp.,
   (b) boiling the milled material to gelatinise any starch and disperse any starch granules,
   (c) hydrolysing starch in the material with amylase,
   (d) precipitating and washing the material with ethanol and freeze drying or spray drying to produce a residue, and
   (e) reconstituting the freeze-dried or spray-dried residue, boiling the reconstituted residue and centrifuging the reconstituted and boiled residue, wherein the supernatant from the centrifugation (e) comprises the substantially starch free soluble fibre; and administering a therapeutically effective amount of the composition to the subject,
   whereby Inflammatory Bowel Disease is treated.

25. The method of claim 24, wherein the composition is in powder form.

26. The method of claim 24, wherein the composition further comprises at least one flavouring, at least one sugar, at least one sweetener, at least one anti-oxidant, at least one mineral, at least one vitamin, or a combination thereof.

27. The method of claim 24, wherein the Inflammatory Bowel Disease is Crohn's Disease.

28. The method of claim 24, wherein the composition further comprises a pharmaceutically acceptable carrier.

29. The method of claim 24, wherein the composition is a liquid, a capsule, or a tablet for oral consumption.

\* \* \* \* \*